(12) United States Patent
Hanson et al.

(10) Patent No.: US 6,242,420 B1
(45) Date of Patent: Jun. 5, 2001

(54) **ELICITOR PROTEIN PRODUCED BY *TRICHODERMA VIRENS* THAT INDUCES DISEASE DEFENSE RESPONSE IN PLANT**

(75) Inventors: Linda E. Hanson, College Station; Charles R. Howell, Bryan, both of TX (US)

(73) Assignee: The United States of America as represented by the Secretary of the Agriculture, Washington, DC (US)

( * ) Notice: Subject to any disclaimer, the term of this patent is extended or adjusted under 35 U.S.C. 154(b) by 0 days.

(21) Appl. No.: 09/573,354

(22) Filed: May 17, 2000

(51) Int. Cl.$^7$ .............................. C07K 5/00; C07K 7/00; A61K 38/00

(52) U.S. Cl. .............................. 514/13; 530/300; 530/326

(58) Field of Search .............................. 514/13; 530/300, 530/326

(56) References Cited

PUBLICATIONS

Hanson, L.E., et al., "Elicitation of cotton phytoalexin production by culture filtrates from *Trichoderma virens*", *Phytopathology*, 89(6), Jun. 1999 (issued May 19, 1999).

Dean, J. F. D., et al., "The Ethylene Biosynthesis–Inducing Xylanase:Its Induction in *Trichoderma viride* and Certain Plant Pathogens", *Phytopathology*, vol. 79, No. 10, 1989, pp. 1071–1078.

Hahn, Michael G., "Microbial Elicitors and Their Receptors in Plants", *Annu. Rev. Phytopathol.*, 34, 1996, pp. 387–412.

*Primary Examiner*—Avis M. Davenport
(74) *Attorney, Agent, or Firm*—M. Howard Silverstein; Randall E. Deck; John D. Fado

(57) ABSTRACT

A novel fungal protein which is effective for inducing or stimulating the defense responses of plants against disease is disclosed. This protein, which is also referred to as an elicitor protein, may be used for the treatment or prevention of fungal infections in plants. The protein is produced by culture of *Trichoderma virens*, and may be subsequently recovered from the culture medium and purified.

12 Claims, No Drawings

SEQUENCE LISTING

<160> NUMBER OF SEQ ID NOS: 1

<210> SEQ ID NO 1
<211> LENGTH: 19
<212> TYPE: PRT
<213> ORGANISM: Trichoderma virens

<400> SEQUENCE: 1

Asp Thr Val Ser Tyr Asp Thr Gly Tyr Asp Asn Gly Ser Arg Ser Leu
 1               5                  10                  15

Asn Asp Val

ELICITOR PROTEIN PRODUCED BY *TRICHODERMA VIRENS* THAT INDUCES DISEASE DEFENSE RESPONSE IN PLANT

BACKGROUND OF THE INVENTION

1. Field of the Invention

The invention relates to a novel elicitor protein for use in stimulating defense responses in plants.

2. Description of the Prior Art

*Trichoderma virens* (formerly known as *Gliocladium virens*) has been recognized as a mycoparasite and antibiotic-producing antagonist of plant pathogens, and has been used as an effective biocontrol agent of several soil-borne root or seedling diseases [Aluko and Hering, 1970, Trans. Br. Mycol. Soc., 55:173–179; Beagle-Ristaino and Papavizas, 1985, Phytopathology, 75:560–564; Howell, 1982, Phytopathology, 72:496–498; Howell and Stipanovic, 1983, Can. J. Microbiol., 29:321–324; Weindling and Fawcett, 1936, Hilgardia, 10:1–16; and Wright, 1956, Plant Soil, 8:132–140]. *T. virens* produces gliotoxin and gliovirin, which are particularly effective antifungal antibiotics, as well as the antibacterial compound heptelidic acid and the antifungal compound viridin.

More recently, efforts have focused on techniques for improving the efficacy of *T. virens* as an antifungal biocontrol agent. These techniques have targeted reducing the production of the phytotoxic agent viridiol by *T. virens*, which may limit its use on valuable crops. Howell has described the addition of sterol inhibiting fungicides to the developing fungus cultures to reduce the production of viridiol (U.S. Pat. No. 5,268,173). Howell has also described the production of mutant strains of T. virens which are deficient for production of viridiol.

SUMMARY OF THE INVENTION

We have now discovered a novel fungal protein which is effective for inducing or stimulating the defense responses of plants against disease. This protein, which is also referred to as an elicitor protein, may be used for the treatment or prevention of fungal infections in plants. The protein is produced by culture of *Trichoderma virens*, and may be subsequently recovered from the culture medium and purified.

In accordance with this discovery, it is an object of this invention to provide a novel elicitor protein for controlling or reducing the severity of plant diseases.

Another object of this invention is to provide a naturally occurring compound which may be used to stimulate the defense responses of plants against disease.

Other objects and advantages of this invention will become readily apparent from the ensuing description.

DETAILED DESCRIPTION OF THE INVENTION

Previously, the antimicrobial activity of *Trichoderma virens* has been attributed to the production of compounds such as gliotoxin, gliovirin, heptelidic acid, and viridin. More recently, chitinase has also been implicated in the biocontrol of cotton seedling disease by *T. virens* (Baek et al., 1999, Curr. Genet., 35:41–50). However, we have unexpectedly discovered an elicitor protein produced by *T. virens* which induces production or activity of defense-related compounds, such as phytoalexins and peroxidase, in plants.

In the following description, the nomenclature used to define the proteins is that specified by Schroder and Lubke ["The Peptides," Academic Press (1965)] wherein, in accordance with conventional representation, the N-terminal appears to the left and the C-terminal to the right. Where the amino acid residue has isomeric forms, it is the L-form of the amino acid that is represented herein unless otherwise expressly indicated.

The mature, native form of the elicitor protein of the invention has a molecular weight of about 18 kDa as determined by sodium dodecyl sulfate polyacrylamide gel electrophoresis (SDS-PAGE). The protein is heat-stable, insoluble in chloroform, and sensitive to treatment with proteinase K but not β-glucosidase. The N-terminal amino acid sequence of the mature form of the natural protein has been determined as DTVSYDTGYDNGSRSLNDV. It is understood that some forms of the protein may have additional N-terminal amino acids which may occur, for example, as a result of incomplete processing or hydrolysis of the signal sequence. The protein may also be covalently bonded to a non-related fusion protein. Further, the protein may be glycosylated. The invention also encompasses substantial equivalents of this protein which retain the ability to elicit production of defense-related compounds in a plant against disease. The practitioner of ordinary skill in the art will recognize that slight deviations of the amino acid sequences may be made without significantly affecting the efficacy of the protein. Substantial equivalents of the above protein include conservative substitutions of amino acids with other amino acids, including either naturally occurring or non-conventional amino acids, which maintain substantially the same charge and hydrophobicity as the original amino acid. Conservative substitutions include for example, replacement of glycine for alanine, valine for isoleucine, leucine for isoleucine, aspartic acid for glutamic acid, lysine for arginine, asparagine for glutamine, phenylalanine for tryptophan, and tryptophan for tyrosine. Examples of conservative substitutions with non-conventional amino acids are described in Rosenberg et al. (U.S. Pat. No. 5,679,782) the contents of which are incorporated by reference herein.

The elicitor protein is produced by a variety of strains of *Trichoderma virens*. Strains of *T. virens* suitable for use herein are typically selected for their ability to increase the synthesis of defense-related compounds in plants. In the preferred embodiment, the strains are screened for their ability to increase synthesis of phytoalexins or to increase peroxidase activity or both. As described in the Examples, seeds or seedlings treated with the strain of interest or its culture supernatant or filtrate, are assayed for production of phytoalexins, such as the terpenoid phytoalexins desoxyhemigossypol and hemigossypol in cotton, or for peroxidase activity. Strains eliciting an increase in the production of one or both of these defense-related compounds in plants treated therewith, relative to untreated controls, are retained as presumptive producers of the elicitor protein. Alternatively, or to confirm presumptive positive strains, the strains may be screened for production of the above-mentioned elicitor protein per se, by assay of the culture media following growth therein. In this embodiment, production of the 18 kDa protein may be confirmed, for example, by sodium dodecyl sulfate polyacrylamide gel electrophoresis (SDS-PAGE).

Optionally, treated seeds or seedlings may also be planted in soil contaminated with a fungal pathogen such as *Rhizoctonia solani* or *Pythium ultimum*. After incubation, the seeds or seedlings are examined for evidence of disease. Strains which are effective to prevent or significantly reduce the incidence or degree of disease (in comparison to untreated controls) are retained for subsequent use in the production of the elicitor protein.

Suitable strains of *T. virens* may be obtained from a wide variety of sources, including but not limited to naturally occurring strains from soil, plant debris, or fungus propagules, or purified isolates. Traditionally, strains of this organism have been separated into one of two broad groups, designated P and Q, based upon gliovirin or gliotoxin production (Howell and Stipanovic, 1991, Petria, 1:129–130, the contents of which are incorporated by reference herein). It is envisioned that strains from either group may be selected for use in this invention. A preferred strain of *T. virens* which produces and secretes extracellular elicitor protein has been retained and has been deposited under the Budapest Treaty in the United States Department of Agriculture Agricultural Research Service Culture Collection (1815 N. University St., Peoria, Ill.), on May 3, 2000, and has been assigned deposit accession number NRRL 30286.

Production of the elicitor protein may be accomplished by culture of any of the aforementioned strains of *T. virens*, isolates or subcultures having the identifying characteristics of those strains, mutants of those strains capable of producing the elicitor protein, or other isolates recovered by the screening procedure described above, by conventional techniques under aerobic conditions that are effective to promote growth. Any number of well-known liquid or solid culture media may be used, although growth on liquid media with agitation is preferred as the protein is secreted into the media and recovery is simplified. Without being limited thereto, one particularly preferred culture media is an aqueous mixture of 5% ground wheat bran with 1% ground peat moss. Examples of other suitable media include media include conventional mycology culture media such as Rawlin Thom medium, potato-dextrose broth, malt extract broth, or 5% millet with 1% peat moss. The fungus will grow and produce elicitor over relatively wide pH and temperature ranges, generally between about 4.0 to 7.5 and 15° to 28° C., respectively, with a pH of about 4.0 and a temperature between about 25–28° C. being preferred. Although the fungus will grow at temperatures above 28° C., yields of the elicitor protein may decrease.

Under cultivation conditions, the elicitor protein is produced concurrently with growth. Once a sufficiently heavy growth of the fungus has been obtained, usually after about 4 days, preferably after 7 days, the soluble elicitor protein may be separated or recovered from the fungus using techniques conventional in the art, such as by centrifugation or filtration. As a practical matter, it is envisioned that commercial formulations of protein may be prepared directly from these crude extracts of the liquid culture medium from which cells have been removed, thereby obviating the need for further purification.

Optionally, the elicitor protein remaining in the culture medium may be further concentrated and purified, particularly for applications demanding a high degree of purity where contamination by other microbial products or culture media components may be undesirable. Suitable techniques for concentration and/or purification of the protein may be readily determined by the practitioner skilled in the art and include, for example, ultrafiltration, freeze-drying, dialysis, ion-exchange chromatography, HPLC size-exclusion chromatography, affinity chromatography, and preferably electrophoresis, particularly SDS-PAGE. Using these techniques, the elicitor protein may be recovered in pure or substantially pure form. When purified by SDS-PAGE, the harsh treatment conditions may denature the protein. Although we have found that the resultant denatured protein is still effective for the purpose of this invention, efficacy is nonetheless reduced. Thus, in the preferred embodiment, protein purified by SDS-PAGE is renatured by treatment with renaturation buffer as is conventional in the art prior to use. Without being limited thereto, details of the preferred culture and separation procedures are described in the Examples.

The protein, either in purified form or contained in the crude, cell-free extracts of culture medium, may be formulated in conjunction with a suitable solid or liquid inert carrier or vehicle as known in the art. The skilled practitioner will recognize that such carriers must be compatible with the protein, and should also be agronomically acceptable. For purified protein, renaturation buffer and water are preferred liquid carriers. The protein may also be formulated with solid inert carriers such as talc, clay or vermiculite. Furthermore, while liquid cell-free extracts of the culture medium could be applied directly upon or to the locus of the plant, seedling or seed to be treated, in the preferred embodiment, the water is removed from these crude extracts to partial or substantial dryness, and the resultant dried mixture broken up or ground into small particles using techniques conventional in the art. Without being limited thereto, suitable water removal techniques include air drying, evaporation or filtration.

In a particularly preferred embodiment, granules of the crude or purified protein are contacted with a sticking agent or adherent as are known in the art to facilitate adherence of the granular product to a target seedling or seed to be treated. Suitable sticking agents may be readily determined by the skilled practitioner and include but are not limited to latex (RHOPLEX B-15, Rohm and Haas, Philadelphia, Pa.), sugars such as sucrose, glucose, fructose, mannose, α-methyl glucoside or corn syrup (as described by Shasha and McGuire, U.S. Pat. No. 5,061,697, issued Oct. 29, 1991, the contents of which are incorporated by reference herein), alginate, methylcellulose, and OPADRY (Colorcon, Inc., Westpoint, Pa.). The sticking agent may be applied onto either the granules or seed prior to use. When seeds are being treated, they may be precoated with elicitor protein prior to sale by the seed supplier, or they may be coated in the field.

In an alternative embodiment, controlled release of the elicitor protein may be accomplished by encapsulation within an inert carrier using conventional techniques. Suitable carriers of this type include but are not limited to alginate gels, wheat-gluten matrices, starch matrices, or synthetic polymers as are known in the art.

Besides the elicitor protein, other additives and adjuncts may be formulated into the subject biocontrol composition. Examples of these include stabilizers such as sucrose, an alkali metal hydrogen phosphate salt, glutamate, gelatin, or casein, inert fillers, UV protectants such as Congo-red, folic acid, paraminobenzoic acid or azobenzene, fertilizers, and pesticides. Particularly preferred for inclusion are fungicides. Without being limited thereto, suitable fungicides include carboxin, pentachloronitrobenzene, or metalaxyl, which are commonly used as cottonseed treatments to control seedling diseases.

To be effective, the elicitor protein must be applied to the locus of, or in the vicinity of, the plant, seedling or seed to be protected. In one preferred embodiment, the protein is applied as a seed treatment coated onto the seeds. In another preferred embodiment, the protein may be applied into the furrows together with the seed during planting. Ideally, particulate formulations of the protein (with or without sticking agent) will be admixed with the seeds in the planter hopper to ensure its application into the furrow in close proximity to the seed. The practitioner skilled in the art will recognize that while the protein could be separately applied to the soil or, in the case of greenhouse plants, added to potting mix of plants grown in greenhouse conditions [Lumsden et al., 1990, Phytopathology, 79:361–366; and Smith et al., 1990, Phytopathology, 80:880–885], such techniques require relatively large amounts of the protein which are impractical in the field.

The subject elicitor protein acts to prevent disease or reduce disease severity by stimulating (increasing) the production defense-related compounds in the treated plant relative to untreated controls. Depending upon the host plant treated, application of the protein to plant seeds, plants or parts may stimulate the production of phytoalexins (such as the terpenoid phytoalexins desoxyhemigossypol and hemigossypol in cotton), or increase peroxidase activity, or both, in the plant, and particularly in its roots. It is also understood that the protein may stimulate other defense responses and the production of other defense-related compounds as well. Accordingly, the protein should be applied in an amount effective to induce at least one such defense-related response for control of a target disease as determined by routine testing. An "effective amount" of the protein is defined herein as those quantities of protein that will result in a significant decrease in the incidence or severity of the plant or seedling disease as compared to an untreated control. The actual effective amount will vary with the disease and causative fungal pathogen, the host plant, the formulation and method of treatment, and environmental conditions, and may be readily determined by the practitioner skilled in the art. When applied as a coating on cotton seeds, preferred concentrations of the protein range from, but are not limited to, greater than about 10 ng/ml, particularly about 20 ng/ml.

The elicitor protein encompassed herein is effective in controlling diseases of a plurality of plants, particularly diseases affecting roots and seedlings. Without being limited thereto, the protein may be applied to any agronomically important plant or its seedling or seed, especially seeds of cotton, cucumbers, beans, and melons.

The following examples are intended only to further illustrate the invention and are not intended to limit the scope of the invention which is defined by the claims.

EXAMPLE 1

Several different strains of *Trichoderma virens* and protoplast fusants were examined for their ability to induce host plant defense responses. Culture filtrates from effective strains were then examined for the same effect.

Materials and Methods

Strains and Culture Methods.

Parent and mutant strains of *T. virens* and other Trichoderma spp., were stored as conidia in 25% glycerol at $-70°$ C. until used. Protoplast fusants were stored on sterile filter paper as mycelium at $-20°$ C. Prior to use, conidia or mycelia were transferred to potato dextrose agar (Difco Laboratories, Detroit, Mich.) plates containing 50 $\mu$g ml$^{-1}$ rifampicin (rifPDA), and colonies developing from them were used as a source of inoculum. The *Rhizoctonia solani* strain used in this study was isolated from a diseased cotton seedling on rifPDA. Dry granular preparations of Trichoderma spp. were made by liquid shake culture (G 10 gyrotory shaker, New Brunswick, N.J.) of the fungus at $27°$ C. for 7 days in a medium consisting of 5% ground wheat bran and 1% ground peat moss adjusted to pH 4.0 with HCl. The cultures were centrifuged (C4–12, Jouan, Inc., Winchester, Va.) and the pellets were air dried and ground to a $\geq 500$ $\mu$m particle size. The preparations were stored at $5°$ C. until used.

The parent, mutant, and fusant strains of Trichoderma spp. used in this work were chosen because of their variability in antibiotic production, mycoparasitism, and suppression of cotton seedling disease incited by *R. solani*. Strains G-6 and G-11 of *T. virens* are effective biocontrol agents that produce gliotoxin and parasitize the hyphae of *R. solani*, while strain G-4 of *T. virens* is a less effective biocontrol agent that parasitizes *R. solani*, but does not produce gliotoxin (Howell et al., 1993, Biocontrol Sci. and Tech., 3:435–441). Mutant strains G6-5 and G6-4 of *T. virens* are both deficient for gliotoxin production and mycoparasitism, but G6-5 is an effective biocontrol agent of cotton seedling disease, while G6-4 is not. The *T. harzianum* strain TH-23 and the *T. koningii* strain TK-7 are the parents, along with G-6, of fusants GTH-34 and GTK-53 and 56, respectively. GTH-34 is an effective biocontrol strain, while GTK-53 and 56 are moderate to low performers as biocontrol agents.

*T. virens* strain G6-5 has been deposited under the Budapest Treaty in the United States Department of Agriculture Agricultural Research Service Culture Collection (1815 N. University St., Peoria, Ill.), on May 3, 2000, and has been assigned deposit accession number NRRL 30286.

*R. solani* AG-4 inoculum was grown as mycelial mats in potato dextrose broth (PDB) still cultures, incubated at $27°$ C. for 5 days. The mats were then aseptically washed, weighed and macerated in a Waring blender (Model 33BL79, Dynamics Corp., New Hartford, Conn.) for 1 min. Inoculum was applied as a 0.0125% (wt/vol) mycelial fragment suspension. *R. solani* inoculum used in the soil flat tests was prepared as previously described (Howell and Stipanovic, 1995, Phytopathology, 85:469–472).

Effect of Seed Treatment on Cotton Seedling Disease Symptoms in Sterile Vermiculite.

Seed of the cotton (*Gossypium hirsutum*) cultivar Stoneville 213 (St 213) were coated with latex sticker (Rhoplex B15J, Rohm and Haas, Philadelphia, Pa.) and dry granular preparations of the effective *T. virens* biocontrol strain G-6 or ineffective mutant G6-4. The control was coated with sterile wheat bran+peat moss preparation (WB+PM). Treated seed were planted in 96 cavity seedling trays containing sterile moist vermiculite, with 10 seeds per treatment, and each treatment was replicated 6 times. The plantings were incubated at $27°$ C. for two days, then 10 ml aliquants of the 0.0125% suspension of *R. solani* mycelial fragments were added to each cavity for one half of the seedlings in each treatment. After a further 2 days incubation, the seedlings in each treatment were harvested and examined for symptoms of disease.

Induction of Terpenoids in Cotton Roots from *T. virens* and *R. solani* Treated Seed.

Stoneville 213 seed coated with latex sticker and dry granular preparations of *T. virens* strain G-6 or WB+PM control were planted in sterile vermiculite seedling trays and incubated as described above. After 3 days, one half of the cavities in each treatment were drenched with 10 ml aliquants of the 0.0125% *R. solani* fragment suspension. After a further 24 hr incubation, the seedlings were harvested and rinsed free of vermiculite, then the roots were excised from the plants. The top 4 cm of the roots in each replication were weighed, cut into 5 mm sections, and soaked for 24 hr in a volume of 90% acetone, 9.9% water, and 0.1% ascorbic acid (3 ml/g of tissue). The acetone extracts were then drawn off with a pipette and subjected to high performance liquid chromatography (HPLC) analysis as previously described (Zhang et al., 1993, J. Phytopathology, 139:247–252, the contents of which are incorporated by reference herein). The HPLC system consisted of a Hewlett Packard Model 1090 liquid chromatograph with a diode array detector set at 235 nm. The solvents, methanol (0.07% $H_3PO_4$) and $H_2O$ (0.07% $H_3PO_4$), were delivered using a gradient starting with 80% $H_2O$, changing to 40% $H_2O$ after 5 min, and ending at 13% $H_2O$ after 22 min. The flow rate was 1.25 ml per min. The hypocotyls from seedlings treated with strain G-6 or the WB+PM control were also extracted and analyzed as described above. All of the above treatments were replicated 3 times, and the experiment was repeated.

Seed of the cotton cultivars Deltapine 50, Deltapine 5409, Coker 312, Acala Maxxa and Rowden were treated with latex sticker and coated with dry granular preparations of *T. virens* strain G-6 or WB+PM control. The treated seed were then planted in sterile moist vermiculite in seedling trays, harvested after 4 days, and extracted and analyzed for terpenoids by HPLC as described above.

Dry, granular WB+PM preparations of the *T. virens, T. koningii, T. harzianum*, and protoplast fusant strains to be used in disease assays were coated on cotton seed with latex sticker. The treated seed were planted in sterile vermiculite seedling trays, incubated, extracted and analyzed for terpenoid synthesis as described above.

Toxicity of Induced Cotton Terpenoids to *R. solani, T. virens* and *T. koningii.*

Authentic samples of the cotton terpenoids desoxyhemigossypol (dHG), hemigossypol (HG), and gossypol (G) were dissolved in dimethyl sulfoxide (DMSO), and aliquants were added to a buffered nutrient solution (Mace et al., Pestic. Biochem. and Physiol., 36:79–82) to make final concentrations of 0–35 $\mu$g ml$^{-1}$, at 5 $\mu$g ml$^{-1}$ intervals. The final DMSO concentration in each was 4%. The buffered nutrient solution contained mycelial fragments of *R. solani, T. virens* or *T. koningii* strains prepared by macerating 5-day old mycelial mats, grown in PDS still cultures, in sterile water with a Waring blender. The macerate was then centrifuged (C4–12, Jouan Inc., Winchester, Va.) at 2,000×g for 10 min, and 0.5 g of the pellet was resuspended in 100 ml of the buffered nutrient solution. Aliquants (0.08 ml) of the terpenoid and DMSO mixtures were added to 1.92 ml lots of the mycelial fragment suspension, 0.4 ml aliquants of the treatments were dispensed into 4 replicate wells of 24-well tissue culture plates, and the plates were incubated for 24 hr at 27° C. The contents of the wells were then spread on the surface of rifPDA plates, incubated at 27° C. for 24 hr, and observed for the presence of mycelial growth.

Biocontrol Efficacy of Trichoderma Species Against Cotton Seedling Disease Incited by *R. solani.*

Seed of the cotton variety St 213 were treated with latex sticker and dry granular WB+PM preparations of *T. virens* parent and mutant strains G-4, G-6, G-11, G6-5, and G6-4, *T. koningii* strain TK-7, *T. harzianum* strain TH-23 and protoplast fusant strains GTK-53, GTK-56 and GTH-34 and planted in flats containing cotton field soil (Lufkin fine sandy loam). Control seed were treated with latex and sterile WB+PM alone. The seeds were planted in 10-seed rows with three replicate rows for each treatment, and the open furrows were evenly sprinkled with 0.1 g per row of *R. solani* inoculum (dry granules of a millet culture diluted 1:9 with ground sterile vermiculite) prior to closure. The flats were watered each day and incubated for 10 days in a growth chamber at 25° C., with a 14 hr photoperiod. Counts of surviving seedlings were made in each treatment in order to calculate % damping-off. Treatments were arranged in a completely randomized design. Biocontrol efficacy was calculated as 100%—% damping-off. The experiment was repeated twice.

Colonization and Penetration of Cotton Roots by Trichoderma Species.

Seeds of the cotton cultivar St 213 were coated with latex sticker and dry granular preparation of *T. virens* strains G-6 and G6-4, *T. koningii* strain TK-7, and the protoplast fusant of G-6 and Tk-7, GTK-56. Seed treated with latex and sterile WB+PM served as a control. The treated seed were planted in sterile moist vermiculite in seedling trays as described above and incubated for 6 days at 27° C. The seedling roots from part of each treatment then had the vermiculite removed manually with a soft brush, and the roots were cut into 5 cm sections and plated on rifPDA. Roots from these same treatments also were washed thoroughly under a stream of RO water, surface sterilized with a solution of 20% chlorox and 10% ethanol for 1 min, rinsed with sterile water and plated in 5 cm sections on rifPDA.

Production of Terpenoid Synthesis Inducer(s) in Liquid Cultures of *Trichoderma virens.*

Supernates obtained from centrifugation (C4-12, Jouan Inc., Winchester, Va.) of 6-day old WB+PM shake cultures of effective strain G-6, noneffective strain G6-4, and WB+PM control were filter sterilized by passage through 0.2 $\mu$m sterile filters (Sterile Acrodisc, A. daigger & Co., Inc., Lincolnshire, Ill.). The filtrates were applied to the radicles of germinated Deltapine 50 (DP-50) seeds by pipetting 3 ml of solution onto the radicles of 12 seeds, when they were 2 cm in length. After 2 days of incubation on moist filter paper in sterile petri dishes at 27° C., the radicles were excised, extracted and analyzed for terpenoid concentration as described above.

Stimulation of Peroxidase Activity.

DP-50 seed, coated with latex and G-6 or WB+PM as previously described, were planted in sterile vermiculite and harvested after 6 days incubation. Six replicate 0.55 g samples of roots or hypocotyls were each ground separately with a glass tissue grinder (Ace glass Inc., Vineland, N.J.) in 1 ml aliquants of 0.1 M phosphate buffer (pH 6.0) and centrifuged (Eppendorf 5415, Brinkmann Instr. Inc., Westbury, N.Y.) at 10,000×g for 5 min. The supernates were assayed for peroxidase activity by the guiacol assay as previously described (Smit et al., Phytochem., 44:811–815).

Statistics.

All experiments were repeated at least once, with similar results, and the data from the last trials are presented here. Statistics were performed using GLM (general linear models; SAS Institute, version 6, Cary, N.C.) or the t-test or correlation functions of EXCEL (Microsoft Corp., Bothell, Wash.).

Results

Induction of Host Resistance and Terpenoid Synthesis.

Of those seedlings grown in vermiculite and infested with *R. solani*, only those from seed treated with *T. virens* G-6 preparations were symptomless. Seedlings from seed coated with the mutant G6-4 or control preparations produced stunted and necrotic radicles. These differences in symptomatology were similar to those observed in nonsterile cotton field soil infested with *R. solani.*

HPLC analyses of seedling radicle extracts for terpenoid content (Table 1) showed that only low levels of dHG, HG and G were present in radicles from seed treated with WB+PM control preparation. Terpenoid concentrations in radicles from control seed infested with *R. solani* for 24 hr were not significantly elevated when compared to the uninfested controls. Radicles from seed treated with *T. virens* strain G-6, however, contained significantly higher levels of dHG, HG and G than the control, while radicles from seed treated with G-6 and infested with *R. solani* contained significantly higher concentrations of dHG and HG than did those treated with G-6 alone (Table 1). Unlike the radicles, hypocotyls from seed treated with G-6 had significantly elevated levels only for dHG compared to the control. HG or G were not significantly different (data not shown).

Analysis of the terpenoid content of radicles from G-6 treated and nontreated seed of the cotton cultivars Deltapine 50, Deltapine 5409, Coker 312, Acala Maxxa and Rowden showed that all varieties, except Deltapine 5409 with dHG, responded to treatment with G-6 by synthesizing significantly higher amounts of dHG, HG and G than did the nontreated controls (Table 2).

Effect of Terpenoids on Growth of *R. solani* and Trichoderma.

Bioassay of the terpenoids induced in *T. virens* treated cotton radicles for toxicity to *R. solani* (Table 3), showed that dHG was the most toxic to *R. solani* ($LD_{100}$=5 $\mu g$ $ml^{-1}$), followed by HG (10 $\mu g$ $ml^{-1}$). G was much less toxic than its precursors, as it did not extensively inhibit growth until 30 $\mu g$ $ml^{-1}$, and it did not give 100% kill at any level tested. *T. virens* strain G-6 was much more resistant to the terpenoid HG than was *R. solani*. HG only achieved significant inhibition of *T. virens* at 25 $\mu g$ $ml^{-1}$, and complete kill at 35 $\mu g$ $ml^{-1}$. Similar to *T. virens*, *T. koningii* strain TK-7 was significantly inhibited at 25 $\mu g$ $ml^{-1}$HG, but complete kill did not occur at any level tested.

Effect of Terpenoid Stimulation on Biocontrol Activity.

Assay of the biocontrol efficacy of strains of *T. virens, T. koningii, T. harzianum* and protoplast fusants (Table 4) in *R. solani* infested cotton field soil flats showed that *T. virens* strains G-6, G-11, G6-5, G-4, and the protoplast fusant GTH-34 significantly reduced seedling damping-off. The *T. harzianum* strain TH-23 and the protoplast fusants GTK-53, and GTK-56 partially reduced seedling damping-off, while the *T. koningii* strain TK-7, the *T. virens* mutant strain G6-4, and the WB+PM control did not control damping-off.

A comparison of the terpenoid concentrations in extracts of cotton radicles treated with Trichoderma strains showing strong ($\geq$60%), weak (40–50%) and no ($\leq$20%) biocontrol activity (Table 4) showed that the effective biocontrol strains stimulated terpenoid production the most, the weak biocontrol strains stimulated an intermediate level, and the ineffective strains stimulated the least. The correlation coefficient calculated with EXCEL for the relationship between disease suppression and terpenoid induction by the 10 strains tested was r=+0.89, and this was determined to be significant ($\alpha$=0.01) by the t-test for $\rho$=0.

Examination of the root segments from seedlings treated with biocontrol effective G-6, ineffective TK-7 and an intermediate fusant GTK-56 showed that all strains colonized the entire root system. Those root systems that were surface sterilized were also colonized in their entirety. The control root systems showed no evidence of Trichoderma infestation.

Effect of Culture Filtrates on Induction of Terpenoid Synthesis and of Seed Treatment on Peroxidase Activity.

Bioassay of the filtrate from WB+PM shake cultures of strain G-6 for induction of terpenoid synthesis in cotton radicles showed that application of the filtrate stimulated terpenoid synthesis. Radicles from WB+PM treated seedlings produced an average of 4.36 $\mu g$ $ml^{-1}$ dHG, 14.89 $\mu g$ $ml^{-1}$ HG, and 133.2 $\mu g$ $ml^{-1}$ G, while those treated with G-6 filtrate produced 26.16 $\mu g$ $ml^{-1}$, 90.58 $\mu g$ $ml^{-1}$ and 250.8 $\mu g$ $ml^{-1}$, respectively (differences are statistically significant at the 95% probability level). Radicles treated with G6-4 filtrate produced only 3.93 g $\mu l^{-1}$dHG, 10.11 $\mu g$ $ml^{-1}$HG, and 129.2 $\mu g$ $ml^{-1}$ G.

Peroxidase activity in hypocotyls from control and G-6 treated seed was not significantly different (P=0.383), but there was significantly (P=0.006) greater activity from roots of G-6 treated seed than there was from roots developed from WB+PM treated seed.

Discussion

The data presented above indicates that treatment of cotton seeds with biocontrol strains of *T. virens* triggers plant defense responses in the developing seedling radicles. A comparison of the biocontrol efficacies of *T. virens, T. koningii, T. harzianum* and protoplast fusant strains with their capacity to induce terpenoid synthesis in treated seedling roots indicates that there is a strong correlation between biocontrol efficacy and induction of terpenoid synthesis in cotton roots. Although biocontrol is almost certainly the culmination of many factors, a major mechanism in the biological control by *T. virens* of cotton seedling damping-off incited by *R. solani* appears to be the induction of host resistance, as indicated here by peroxidase activity and terpenoid synthesis, in seedling roots by the biocontrol agent prior to attack by the pathogen. Terpenoid synthesis is even further enhanced by subsequent pathogen attack. Penetrating pathogen hyphae are, therefore, met by increased concentrations of bioactive compounds, and subsequent development of the fungus is suppressed.

Assay of *T. virens* culture filtrate for terpenoid induction, indicates that the inducers are synthesized by the fungus and released to the environment.

EXAMPLE 2

Crude cell-free culture filtrate of *T. virens* was examined for its effect on peroxidase activity in cotton and cucumber seedlings. *T. virens* strain G-6 was cultivated by liquid shake culture for 7 days as described in Example 1. The resultant culture medium was then filtered to remove all cells of the fungus as described in Example 1, and the sterile culture filtrate was retained. This crude culture filtrate was applied onto the seedlings of cotton and cucumbers. After incubation, the seedlings were examined for peroxidase activity as described in Example 1. In treated cotton seedlings, the peroxidase activity was 11.77 pmoles/sec, significantly higher than that observed in the untreated controls which was 8.72 pmoles/sec (P=0.006, by t-test). A similar increase in peroxidase activity was observed in treated cucumber seedlings. In treated cucumber seedlings, the peroxidase activity was 24.90 pmoles/sec, while the activity in the untreated controls was 16.84 pmoles/sec (P=0.014, by t-test).

EXAMPLE 3

*T. virens* strain G-6 was cultivated by liquid shake culture for 7 days as described in Examples 1 and 2. The resultant culture medium was then filter sterilized, and the cell-free culture filtrate was retained. The culture filtrate was put through 10 K molecular weight-cut-off filter, and then run on 15% polyacrylamide gel using SDS-PAGE under denaturing conditions. The approximately 18 kDa band and a randomly selected band greater than 30 kDa were excised and electroeluted or eluted by incubation in an elution buffer after homogenization of the gel slices followed by centrifugation. The eluted materials were tested for activity (i.e., stimulation of phytoalexin production) on cotton radicles as described in Example 1. The elution buffer was used as the control.

Upon analysis, the concentration of dHG (the first compound in gossypol pathway) was 3.80±0.22 µg/g tissue from buffer-treated radicles, 3.93±0.20 µg/g tissue from radicles treated with a randomly selected protein band (>30 kDal) and 7.37±0.14 µg/g tissue from radicles treated with the electroeluted 18 kDal band. Thus, the 18 kDal band gave significantly higher dHG levels than the other two treatments at a 95% probability. These results demonstrate that the compound comprising the 18 kDal band protein is effective for stimulating the production of defense related compounds.

The compound comprising 18 kDa band was found to be heat stable, insoluble in chloroform, and sensitive to treatment with proteinase K but not β-glucosidase, suggesting that the active agent is a protein. The 18 kDa protein was subjected to amino-terminal amino acid sequence analysis, and the first 19 amino acids at the amino terminus were determined to be DTVSYDTGYDNGSRSLNDV.

It is understood that the foregoing detailed description is given merely by way of illustration and that modifications and deviations may be made therein without departing from the spirit and scope of the invention.

TABLE 1

Effect of *Trichoderma virens* on terpenoid concentrations in cotton roots inoculated with *Rhizoctoniia solani*

| Treatment | Terpenoids (µg/g tissue)[a] | | |
|---|---|---|---|
| | HG | dHG | G |
| NT Control[b] | 1.58 a[c] | 1.75 a | 33.30 a |
| R. solani | 4.00 a | 3.33 a | 29.00 a |
| T. virens | 29.30 b | 13.97 b | 109.26 b |
| T. virens + R. solani | 39.78 c | 22.62 c | 94.84 b |

[a]HG = hemigossypol, dHG = desoxyhemigossypol, G = gossypol; these terpenoids are found in extracts of cotton seedling roots.
[b]NT = nontreated.
[c]Means followed by different letters are significantly different according to the protected least significant difference (LSD) test at = 0.05 using GLM (general linear models; SAS Institute, Cary, NC).

TABLE 2

Effect of seed treatment with *Trichoderma virens* on terpenoid levels in seedling radicles of five cotton varieties

| Cotton varieties | Terpenoids (µg/g tissue)[a] | | |
|---|---|---|---|
| | HG | dHG | G |
| Deltapine-5409-C[b] | 17.30 | 7.20 | 242.98 |
| Deltapine-5409-T[b] | 42.29**[c] | 9.33 | 533.99** |
| Coker-312-C | 7.57 | 10.19 | 80.35 |
| Coker-312-T | 23.87** | 22.89** | 253.23** |
| Deltapine-50-C | 10.57 | 11.53 | 103.65 |
| Deltapine-50-T | 39.98** | 36.16** | 293.80** |
| Acala Maxxa-C | 13.44 | 9.90 | 263.93 |
| Acala Maxxa-T | 31.97** | 16.15** | 349.26* |
| Rowden-C | 19.34 | 10.27 | 223.53 |
| Rowden-T | 51.36** | 22.20** | 362.00* |

[a]Numbers given are average concentrations. HG, dHG and G are the terpenoids hemigossypol, desoxyhemigossypol, and gossypol, respectively.
[b]C = control seed coated with sterile wheat bran + peat moss; T = seed coated with *T. virens* wheat bran + peat moss preparation.
[c]*Treatment means are significantly different from the control means as assessed by Student's t test ( = 0.05); **( = 0.01).

TABLE 3

Effects of terpenoids from cotton roots on the growth of *Rhizoctonia solani* and of hemigossypol (HG) on strains of *Trichoderma virens* and *T. koningii*

| Concentration (µg ml$^{-1}$) | dHG[a] | HG | Tv | Tk | G |
|---|---|---|---|---|---|
| 1 | +[b] | + | + | + | + |
| 2.5 | + | + | + | + | + |
| 5 | − | + | + | + | + |
| 7.5 | − | + | + | + | + |
| 10 | − | − | + | + | + |
| 12.5 | − | − | + | + | + |
| 15 | − | − | + | + | + |
| 20 | − | − | + | + | + |
| 25 | − | − | +− | +− | + |
| 30 | − | − | +− | +− | +− |
| 35 | − | − | − | +− | +− |

[a]dHG, HG, and G are the cotton terpenoids desoxyhemigossypol, hemigossypol and gossypol, respectively. Tv = *Trichoderma virens* strain G-6 and Tk = *Trichoderma koningii* strain TK-7.
[b]+ = mycelial growth after 24 hr incubation; − = no mycelial growth.; +− = mycelial growth inhibited.

TABLE 4

Induction of terpenoid synthesis in cotton roots by Trichoderma spp. and their efficacy as biocontrol agents of *Rhizoctonia solani*-induced cotton seedling disease

| Treatment[x] | Terpenoids (µg/g root) | | | | % Disease |
|---|---|---|---|---|---|
| | HG[y] | dHG | G | Total | |
| NT cont. | 10.0 gh[z] | 5.4 de | 42.9 de | 58.3 de | 80 de[z] |
| TK-7[3] | 19.2 def | 7.4 bc | 40.2 de | 66.8 de | 90 e |
| G6-4 | 14.1 efg | 7.0 cd | 48.0 de | 69.0 de | 80 de |
| GTK-56 | 13.6 fgh | 4.6 e | 47.9 de | 66.1 de | 67 cde |
| TH-23 | 19.9 de | 7.2 c | 49.1 de | 76.2 d | 50 abcd |
| GTK-53 | 34.0 a | 11.4 a | 60.0 d | 105.4 c | 50 abcd |
| G-4 | 21.5 cd | 8.0 bc | 83.1 c | 112.6 bc | 40 abc |
| G-6 | 27.2 bc | 8.9 b | 107.2 ab | 143.3 a | 37 abc |
| G-11 | 32.0 ab | 8.0 bc | 121.0 a | 161.0 a | 30 ab |
| GTH-34 | 33.6 a | 7.7 bc | 93.4 bc | 134.6 ab | 30 ab |
| G6-5 | 33.5 a | 11.5 a | 94.4 bc | 139.4 ab | 17 a |

[x]G-4, G-6 and G-11 are *T. virens* strains; G6-4 and G6-5 are mutant strains of G-6. TK-7 is a *T. koningii* strain, and TH-23 is a *T. harzianum* strain. GTK-53 and GTK-56 are protoplast fusants of G-6 and TK-7. GTH-34 is a protoplast fusant of G-6 and TH-23.
[y]HG, dHG, and G are the cotton terpenoids hemigossypol, desoxyhemigossypol and gossypol, respectively.
[z]Means in a column followed by different letters are significantly different according to the protected least significant difference (LSD) test at µ = 0.05 using GLM (general linear models; SAS Institute, Cary, NC).

We claim:

1. An isolated protein comprising the amino acid sequence:

DTVSYDTGYDNGSRSLNDV or a substantial equivalent thereof, said protein being effective for stimulating phytoalexin production or increased peroxidase activity or both in plants.

2. The isolated protein of claim 1 wherein said protein is from *Trichoderma virens* and has a molecular weight of about 18 kDa as determined by sodium dodecyl sulfate polyacrylamide gel electrophoresis.

3. The isolated protein of claim 2 wherein said amino acid sequence is an N-terminal amino acid sequence.

4. The isolated protein of claim 1 wherein said protein is pure.

5. A method for controlling plant disease comprising applying a composition which comprises a protein, said protein comprising the amino acid sequence:

DTVSYDTGYDNGSRSLNDV or a substantial equivalent thereof, in an amount effective for stimulating phytoalexin production or increased peroxidase activity or both in plants, to the locus of a plant, seedling or seed.

6. The method as described in claim 5 wherein said applying comprises applying said composition onto a seed.

7. The method as described in claim 6 wherein said seed is the seed of a plant selected from the group consisting of cotton, cucumbers, beans, and melons.

8. The method of claim 7 wherein said protein is substantially pure.

9. The method of claim 5 wherein said composition is free of cells of *Trichoderma virens*.

10. The method of claim 5 wherein said protein is from *Trichoderma virens* and has a molecular weight of about 18 kDa as determined by sodium dodecyl sulfate polyacrylamide gel electrophoresis.

11. The method of claim 5 wherein said amino acid sequence is an N-terminal amino acid sequence.

12. A method for controlling plant disease comprising applying a cell-free culture medium produced by the culture of *Trichoderma virens* effective for producing a protein effective for stimulating phytoalexin production or increased peroxidase activity or both in plants, to the locus of a plant, seedling or seed.

* * * * *